United States Patent [19]
Aoyagi et al.

[11] Patent Number: 5,278,627
[45] Date of Patent: Jan. 11, 1994

[54] APPARATUS FOR CALIBRATING PULSE OXIMETER

[75] Inventors: Takuo Aoyagi; Masayoshi Fuse; Yoshiaki Shindo; Masayuki Kato, all of Tokyo, Japan

[73] Assignee: Nihon Kohden Corporation, Tokyo, Japan

[21] Appl. No.: 835,505

[22] Filed: Feb. 14, 1992

[30] Foreign Application Priority Data

Feb. 15, 1991 [JP] Japan .................................. 3-043001

[51] Int. Cl.⁵ ............................................. G01N 33/48
[52] U.S. Cl. ....................................... 356/41; 356/42; 356/243; 250/252.1; 128/633; 128/691
[58] Field of Search .......................... 356/41, 42, 243; 250/252.1; 128/633, 691

[56] References Cited

U.S. PATENT DOCUMENTS

4,834,532  5/1989  Yount ................................. 356/42

Primary Examiner—Davis L. Willis
Assistant Examiner—LaCharles Keesee
Attorney, Agent, or Firm—Sughrue, Mion, Zinn, Macpeak & Seas

[57] ABSTRACT

An apparatus for calibrating a pulse oximeter which can improve the repetitivity of measured values for calibration tests and which can calibrate the pulse oximeter with a high reliability. A tissue model having a light-absorbing characteristic approximated to that of the tissue of a living body is inserted into a space between a light-emitting section and a light-receiving section of a measuring probe that is connected to the pulse oximeter, and a blood model having a light-absorbing characteristic that is approximated to that of the blood is moved within the tissue model so as to enter into or exit from the space between the light-emitting section and the light-receiving section.

6 Claims, 8 Drawing Sheets

APPARATUS FOR CALIBRATING PULSE OXIMETER

BACKGROUND OF THE INVENTION

The invention relates to an apparatus for calibrating a pulse oximeter using a finger model approximated to a light-absorbing characteristic of a human finger.

Description of the Related Art

A pulse oximeter injects light rays of, e.g., two different wavelengths, each of which exhibits a different light-transmitting characteristic to oxygenated hemoglobin and reduced hemoglobin into the finger tip, etc., of a human being, calculates a ratio between variations of the transmitted light rays of the respective two wavelengths appearing as the arterial blood pulsates, and finds the degree of oxygen saturation of the circulating blood with this ratio as a function.

By the way, a method of calibrating this pulse oximeter has conventionally involved only the oximeter body, not including a measuring probe, and calibrations have been made electrically.

Another method calibrates the pulse oximeter by actually making a measurement on the finger tip of a healthy human being. The reliability of the calibration is judged by comparing such measurement with a plurality of measurements made with the finger tip of the same person installed to the measuring probe and then checking that the compared measurements are the same.

However, in the calibration method involving the actual measurement of the finger tip of a human being, the repetitivity of the measured value is so poor that it is difficult to judge whether the measured value is reliable or not.

SUMMARY OF THE INVENTION

The invention has been proposed to overcome such a conventional problem. Accordingly, an object of the invention is to provide an apparatus for calibrating a pulse oximeter which can improve the repetitivity of a measured value for calibration tests and which can calibrate the pulse oximeter with a high reliability.

To achieve the above object, an apparatus for calibrating a pulse oximeter of the invention is characterized as including: a tissue model which has a light-absorbing characteristic approximated to that of a living body and which is inserted into a space between a light-emitting section and a light-receiving section of a measuring probe connected to the pulse oximeter; and a blood model which has a light-absorbing characteristic approximated to that of the blood and which moves within the tissue model so as to enter into or exit from the space between the light-emitting section and the light-receiving section.

Further, the apparatus for calibrating a pulse oximeter in which the profile of an end surface of the blood model is curved so as to depict an arc on the light-emitting section side, the end surface being a side entering into the space between the light-emitting section and the light-receiving section.

According to the first aspect of the invention, the blood model is moved within the tissue model, whereby the light-absorbing characteristic approximated to pulsation of the blood within the living body can be simulated.

Further, according to the second aspect of the invention, the profile of an end surface of the blood model is curved, whereby a light-receiving output detected by the light-receiving section can be simulated as a signal waveform analogous to pulse waves of the living body when the blood model is moving so as to traverse the space between the light-emitting section and the light-receiving section.

BRIEF DESCRIPTION OF THE DRAWINGS

FIGS. 10(a) through (k) are timing diagrams showing an operation of processing signals within the pulse oximeter;

DETAILED DESCRIPTION OF THE PREFERRED EMBODIMENTS

Figure 1:
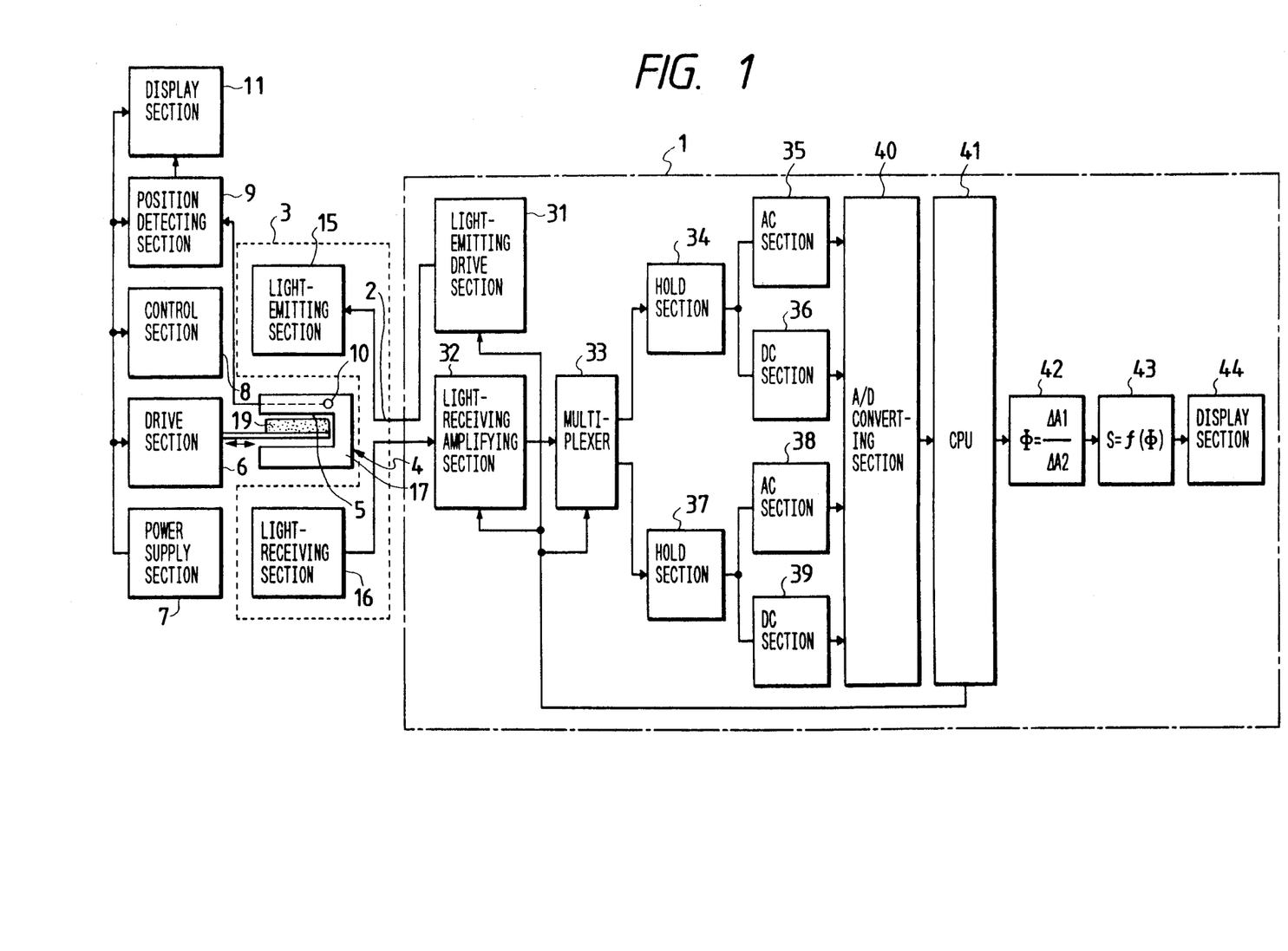
FIG. 1 is a block diagram showing an apparatus for calibrating a pulse oximeter, which is an embodiment of the invention, together with the pulse oximeter.

An apparatus for calibrating a pulse oximeter, which is a specific embodiment of the invention, will be described in detail with reference to the drawings. FIG. 1 shows a block diagram of the apparatus for calibrating a pulse oximeter.

In FIG. 1, a model 4 representing a human finger is installed to a measuring probe 3 that is connected to a pulse oximeter body 1 through a signal cable 2, and a pulsation generating section 5 constituting a part of the finger model 4 is driven by a drive section 6 so as to shuttle within the finger model 4. The drive section 6 is supplied with driving power from a power supply section 7 and receives from a control section 8 such a control signal as to drive the pulsation generating section 5 at an appropriate speed. Further, a position detecting section 9 detects a position of the pulsation generating section 5 based on an input signal from a sensor 10, and the detection result is displayed on a position detection display section 11.

Figure 2:
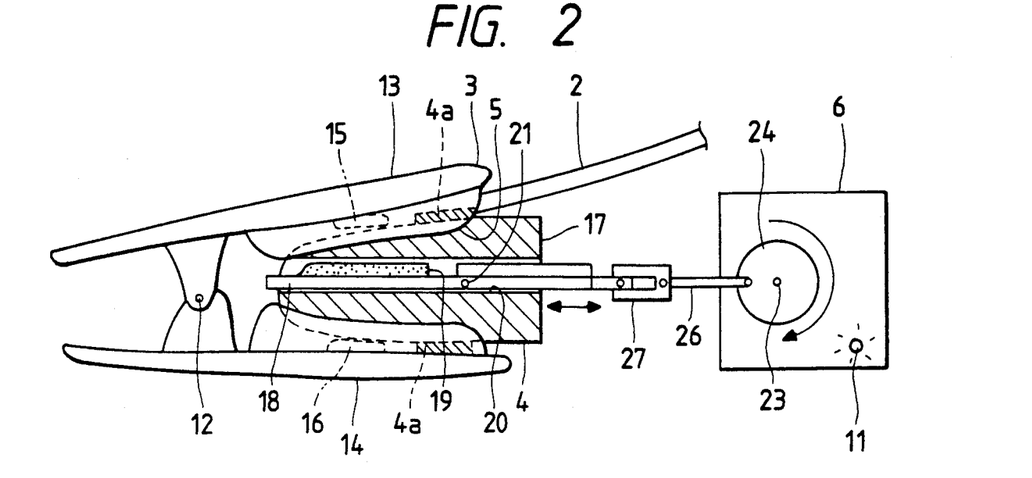
FIG. 2 is a sectional view showing a finger model of the present invention that is installed to a measuring probe.

As shown in FIG. 2, the measuring probe 3 is biased by a spring so that its upper clamp plate 13 and its lower clamp plate 14 are closed inward, both clamp plates being freely opened and closed with a pin 12 acting as a pivot, and on an internal surface portion of this upper clamp plate 13 is a light-emitting section 15, which consists of two light-emitting diodes, while on an the internal surface portion of the lower clamp plate 14 is a light-receiving section 16 so as to confront the light-emitting section 15. The two light-emitting diodes emits light rays having wavelengths λ1, λ2 which are different from each other and used to measure the degree of oxygen saturation.

Figure 3:
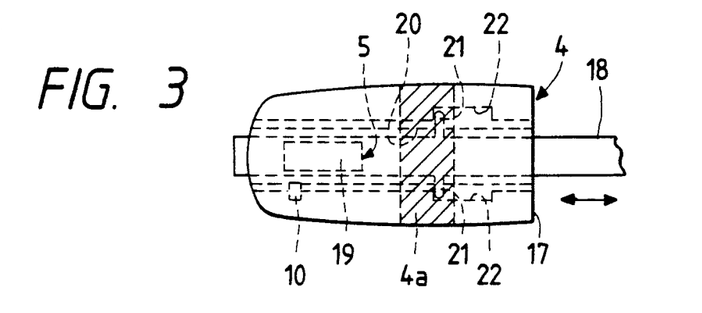
FIG. 3 is a plan view of the finger model.
Figure 4:
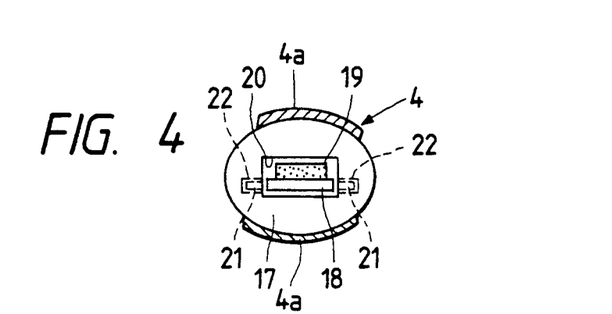
FIG. 4 is a front view of the finger model.

The finger model 4 installed into a space between the upper clamp plate 13 and the lower clamp plate 14 of the measuring probe 3 during a calibration is made up of a tissue model 17 and the pulsation generating section 5 which is moved within the tissue model 17. The tissue model 17 is made of, e.g., polystyrene resin and has predetermined light-absorbing characteristics to the respective wavelengths so as to be analogous to the tissue of a living body. An insertion hole 20 is arranged along the length of the tissue model 17 so that the pulsation generating section 5 formed by bonding a blood model 19 on a light-transmitting substrate 18 can be inserted thereinto. On both side walls of the substrate 18 are slide guide pins 21, 21 arranged as shown in FIGS. 3 and 4, and these guide pins 21, 21 are fitted into slide grooves 22, 22 formed on both side portions of the insertion hole 20, so that the pulsation generating section 5 can be moved within the tissue model 17 in a range defined by the slide groove 22.

A disk 24 is secured to the output shaft 23 of a motor constituting the drive section 6, and a coupling rod 26 is rotatably mounted at an eccentric position of the disk 24. A tip of the coupling rod 26 is connected to the base of the substrate 18 of the pulsation generating section 5 through a rotatable coupling 27. Accordingly, a rotary motion of the motor is transmitted to the pulsation generating section 5 through the disk 24 as a linear motion to further cause the pulsation generating section 5 to shuttle back and forth within the finger model 4 in such a manner as to enter into and exit from the space between the light-emitting section 15 and the light-receiving section 16.

Further, the tissue model 17 is provided with the sensor 10, which verify that the finger model 4 is correctly interposed between the light-emitting section 15 and the light-receiving section 16 when the finger model 4 is installed to the measuring probe 3. A detection output is sent from this sensor 10 upon reception of light rays of the light-emitting section 16, and the position detection section 9 turns on the display section 11 made up of light-emitting diodes in accordance with the sensor detection signal. Therefore, by checking the lighting condition of the display section 11, whether the finger model 4 has been installed correctly to the probe 3 can be verified. Slip protection members 4a, 4a are bonded to an upper surface portion and an lower surface portion of the finger model 4.

Figure 5:
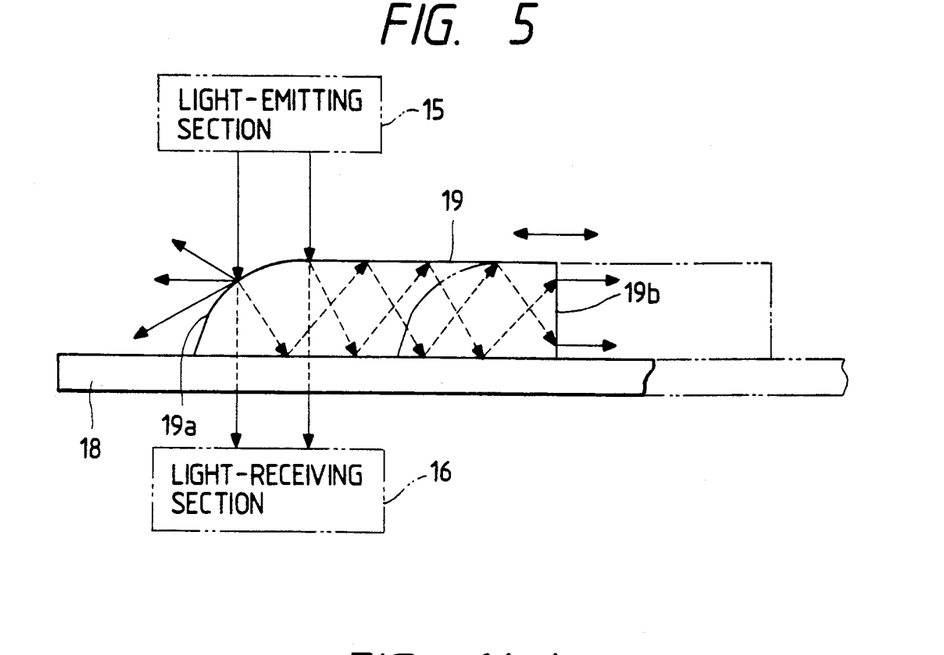
FIG. 5 is a diagram illustrative of both a profile of a blood model used in the finger model and a state in which light rays passing through the blood model are being scattered.
Figure 9:
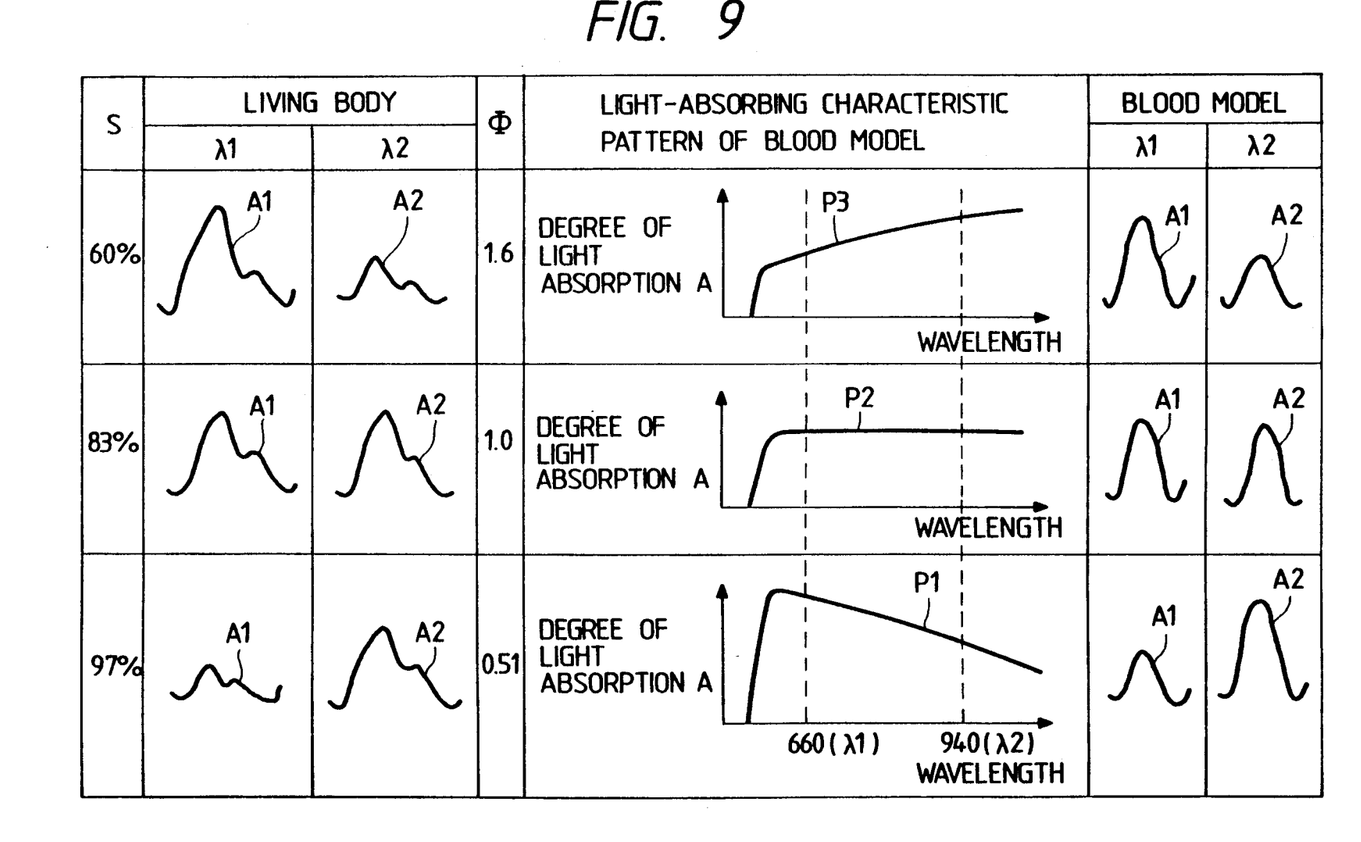
FIG. 9 is a diagram showing light-absorbing characteristic patterns of blood models, each of which is used to calibrate different degrees of oxygen saturation.

The blood model 19 on the substrate is formed into a plate-like member, by an injection molding method, by mixing a powdery orange fluorescent material within a range between 50-75% and a powdery red fluorescent material within a range between 50-25% with an acrylic as a base to impart a light-absorbing characteristic which is analogous to the blood. The present invention employs the fluorescent material, for example, ORANGE 240 and RED 300 of Lumogen F tradename of a compound manufactured from BASF. This fluorescent material is the compound known as Perylen. The blood model 19 is constituted by changing the ratio between the red and orange fluorescent material within the range described above so that the blood model 19 has light-absorbing characteristic patterns P1, P2 and P3 of the blood model, as shown in FIG. 9, for calibrating different degrees of oxygen saturation. At this time, when the range of orange fluorescent material is increased, the blood model has a light absorbing characteristic pattern for calibrating degree of oxygen saturation being in high. An end portion 19a of the blood model 19 is out out into such a profile as to have a curved section as shown in FIG. 5. By giving such a curved section to the end portion of the blood model 19, a detection waveform close to a pulse wave of a living body can be extracted from the light-emitting section 15 when the blood model 19 moves in and out of the space between the light-emitting section 15 and the light-receiving section 16 as shown by the solid lien and the phantom line. If the end of the blood model 19 has a right-angled cutout, a detection waveform so steep as a rectangular wave that it is different from the pulse wave of a living body is outputted. Here, the blood model 19 is surface-treated so that a light-absorbing characteristic analogous to scattering of transmitted light rays within the living body, so that straight light rays injected into the blood model 19 and scattering light rays generated within the model 19 are re-emitted while converted into fluorescent light rays having a long wavelength. The majority of the re-emitting light rays are induced to an edge portion 19b by total reflection as shown by the broken line. while the remaining transmitted light rays are utilized for pulsation detection. The induction of the majority of light rays to the edge portion 19b allows a larger signal level difference caused by fluctuation of the pulsation to be obtained.

This blood model 19 is removably, so that when its light-absorbing characteristic is changed due to contamination or the like, it can be replaced.

Figure 6A:
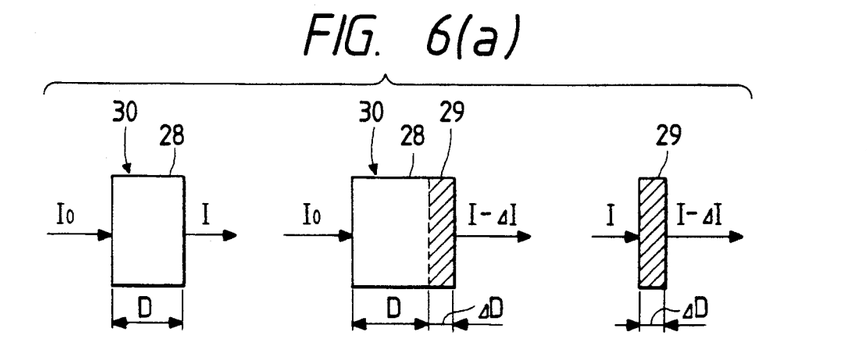
FIGS. 6(a) and (b) are schematic diagrams illustrative of a living body and a light-absorbing characteristic of the finger model.
Figure 6B:
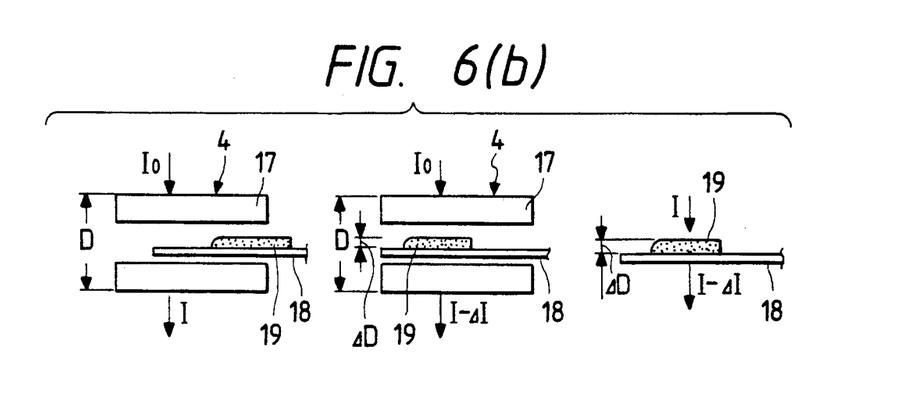

FIGS. 6(a) and (b) are diagrams in which a living body and the finger model 4 are compared in schematic form in an attempt to explain the light-absorbing characteristic of an actual living body and that of the finger model 4; FIG. 6(a) presents schematics of a living body 30 divided into a tissue layer 28 and a blood layer 29; and FIG. 6(b) presents schematics of the finger model 4. In FIGS. 6(a), (b), reference character D designates the thickness of the tissue; $\Delta D$, the thickness of the blood; $I_0$, the amount of injected light; I, the amount of light transmitted through the tissue; and $(I - \Delta I)$, the amount of transmitted light obtained by subtracting the amount of light reduced in the blood resulting from pulsation. By moving the blood model 19 within the tissue model 17 in this way, the light-absorbing characteristic approximated to the characteristic of the living body 30, in which the degree of light absorption is varied as the blood pulsates, can be simulated by the finger model 4.

Here, if it is assumed that $\Delta A$ is the increment of the degree of light absorption resulting from the pulsation, E is the light-absorbing coefficient of a light-absorbing substance. and C is the density of the light-absorbing substance, then $\Delta A$ can be given by the following equation.

$$\Delta A = \text{Log}\,[I/(I-\Delta I)] = EC\Delta D$$

And if it is assumed that $\Delta A1$, $\Delta A2$ are the increments of the degree of light absorption in the first and second wavelengths $\lambda 1$, $\lambda 2$, respectively, and E1, E2 are the light-absorbing coefficients of the light-absorbing substance, then the ratio $\phi$ between the light-absorbing coefficients can be given by the following equation.

$$\phi = \Delta A1/\Delta A2 = E1/E2$$

With the ratio $\phi$ as a function, the degree of oxygen saturation S can be obtained with the following equation.

$$S = f(\phi)$$

Figure 7:
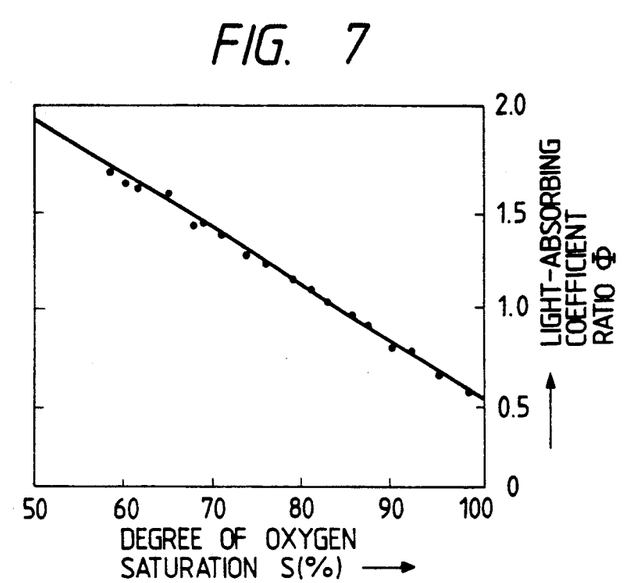
FIG. 7 is a graph showing the degree of oxygen saturation of a human finger tip related to the light-absorbing coefficient ratio $\phi$.

FIG. 7 shows an S-$\phi$ relation curve with respect to the finger tip of a human being. Since the finger model 4 must provide a characteristic approximated to this S-$\phi$ relation curve, materials of the tissue model 17 and the blood model 19 are so selected as that such a characteristic can be obtained.

Figure 8:
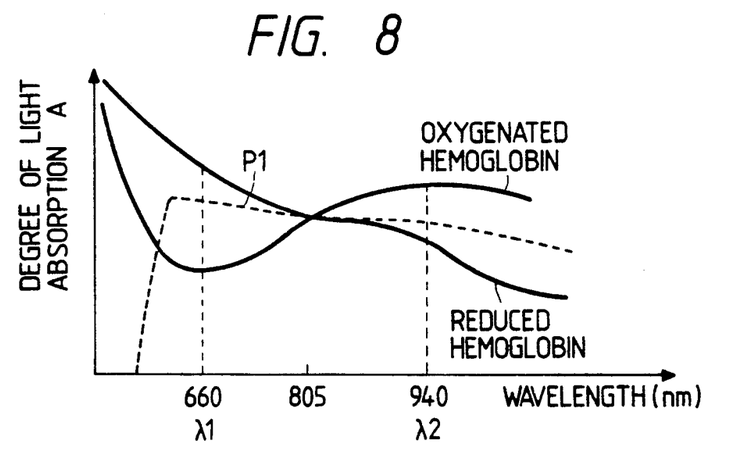
FIG. 8 is a characteristic diagram showing a light-absorbing characteristics of oxygenated hemoglobin and reduced hemoglobin and a light-absorbing characteristic of the blood model.

FIG. 8 shows light-absorbing characteristics of oxygenated hemoglobin and reduced hemoglobin as well as a light-absorbing characteristic pattern P1 of the blood model 19 when the finger model 4 is used as a simulator so that a calibration test can be conducted with the degree of oxygen saturation being at 97%.

Further, FIG. 9 shows light-absorbing characteristic patterns of the blood model 19 when the blood model 19 is used as a simulator with the degrees of oxygen saturation being at 83% and 60%. In FIG. 9, A1, A2 on the right side indicate pulsation-varied waveforms (simulated sine waves) at degrees of light absorption measured on blood models 19 corresponding to the respective light-absorbing characteristic patterns P1, P2, P3 when the wavelengths are $\lambda 1$, $\lambda 2$, while A1, A2 on the left side indicate pulsation-varied waveforms at degrees of light absorption measured on the living body, respectively.

An operation of processing a signal within the pulse oximeter when a calibration test is conducted with the finger model 4 installed to the measuring probe 3 will be described next with reference to a timing diagram shown in FIGS. 10(a) through (k).

Figure 10:
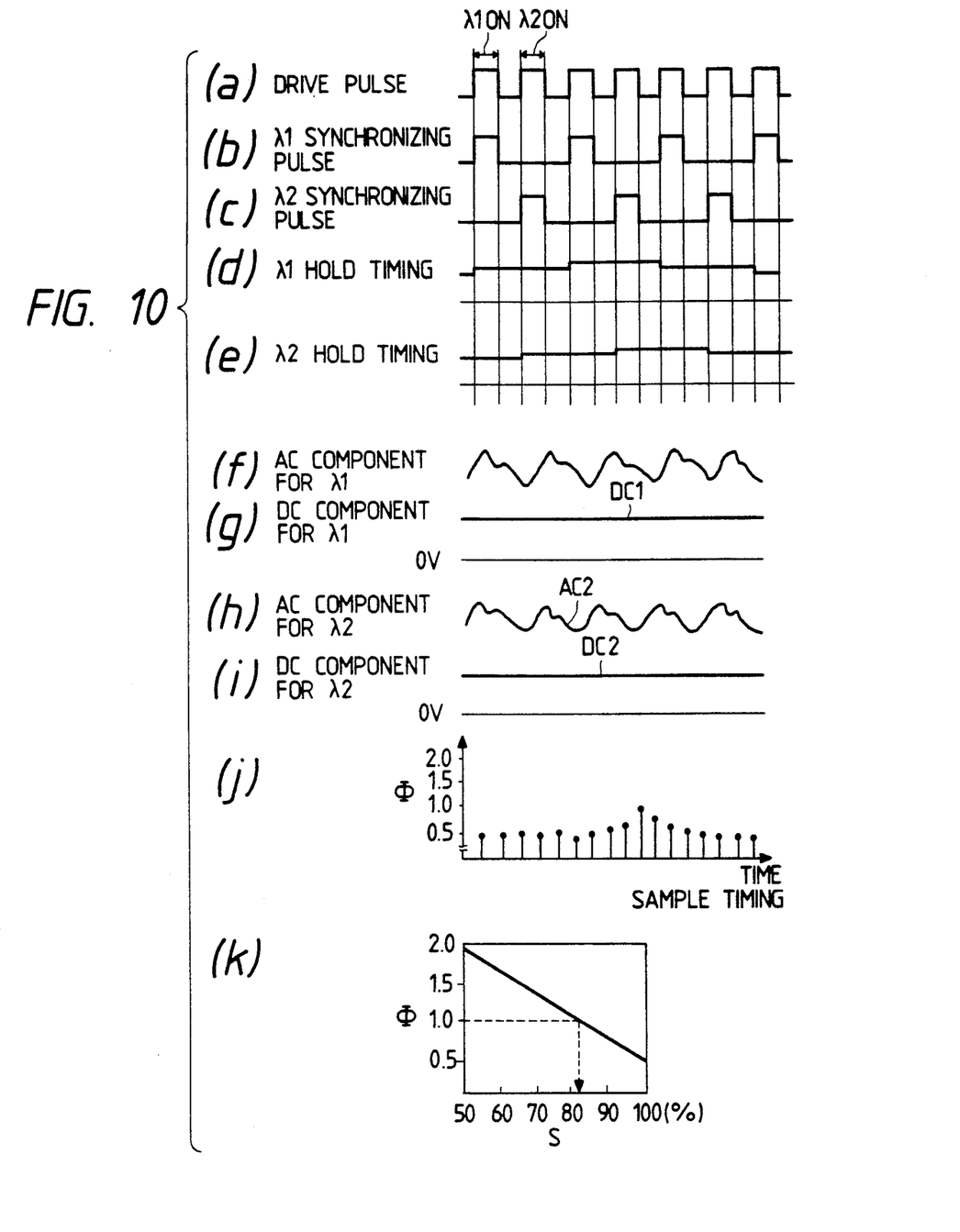

First, a drive pulse (a) is outputted to turn on the light-emitting diodes of the light-emitting section 15 corresponding to the wavelengths $\lambda 1$, $\lambda 2$, respectively, from a light emission drive section 31, so that the two light-emitting diodes are turned on alternately in synchronism with the drive pulse. The light rays emitted from the light-emitting section 15 are received by the light-receiving section 16 after having passed through the finger model 4, and an output from the light-receiving section 16 is supplied to a light-receiving amplifier 32. The light-receiving signal amplified at the amplifier 32 is sent to a multiplexer 33, where it is separated into signals corresponding to the respective wavelengths based on a $\lambda 1$ synchronizing pulse (b) and a $\lambda 2$ synchronizing pulse (c).

With respect to the separated signals outputted from the multiplexer 33, the signal for $\lambda 1$ is held at a hold section 34, and not only an AC component AC1 (f) corresponding to an increment of the pulsation is extracted at a subsequent AC section 35, but also a DC component DC1 (g) corresponding to the tissue is extracted by a DC section 36. Further, the signal for $\lambda 2$ is held by a hold section 37, and not only an AC component AC2 (h) corresponding to an increment of the pulsation is extracted at a subsequent AC section 38, but also a DC component DC2 (i) corresponding to the tissue is extracted by a DC section 39.

Output signals from the AC sections 35, 38, and the DC sections 36, 39 are converted into digital signals by an A/D converting section 40, fed to a CPU 41 thereafter to calculate increments $\Delta A1$, $\Delta A2$ of the light-absorbing lengths corresponding to the respective wavelengths $\lambda 1$, $\lambda 2$ as shown by the following equations.

$$\Delta A1 = AC1/DC1$$

$$\Delta A2 = AC2/DC2$$

A subsequent arithmetic and logic processing section 42 successively calculates the ratio $\phi$ between the light-absorbing coefficients as shown by the following equation.

$$\phi = \Delta A1/\Delta A2$$

The degree of oxygen saturation S is calculated by a subsequent arithmetic and logic processing section 43 from this ratio $\phi$ between the light-absorbing coefficients, and the value of the calculated degree of oxygen saturation $\delta$ is displayed on a display section 44.

A finger model 4 of a calibration apparatus, which is another embodiment of the invention shown in FIGS. 11 and 12, will be described next. In this embodiment, the pulsation generating section 5 is not caused to shuttle within the tissue model 17 as in the above-mentioned embodiment, but a pulsation generating section 48 is rotated to thereby simulate pulsation of a living body.

Figure 11:
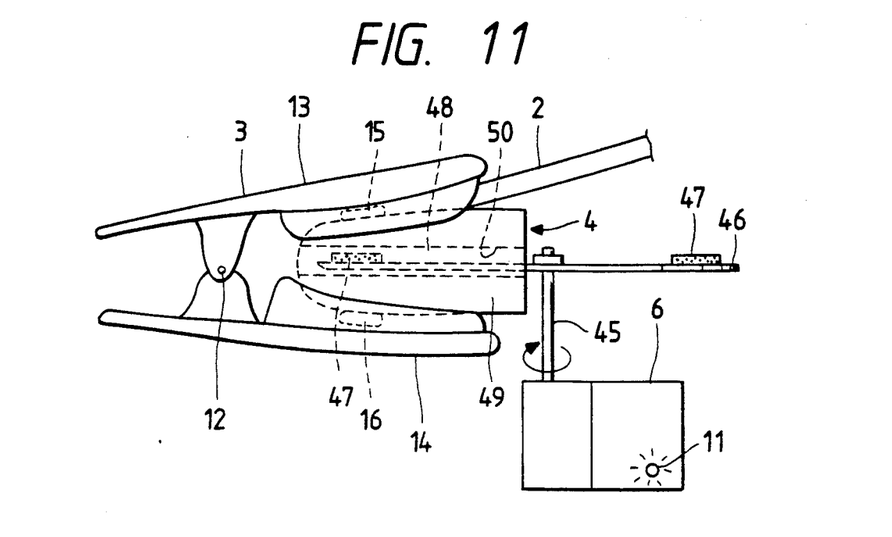
FIG. 11 is a side view showing a finger model of a calibration apparatus, which is another embodiment of the present invention.
Figure 12:
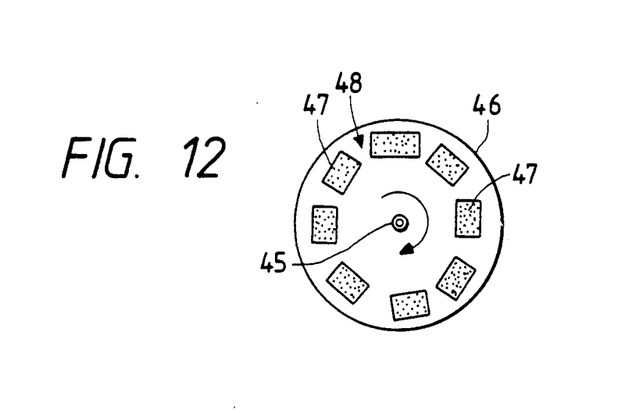
FIG. 12 is a plan view of a pulsation generating section used for the finger model of the embodiment shown in FIG. 11.
Figure 13:
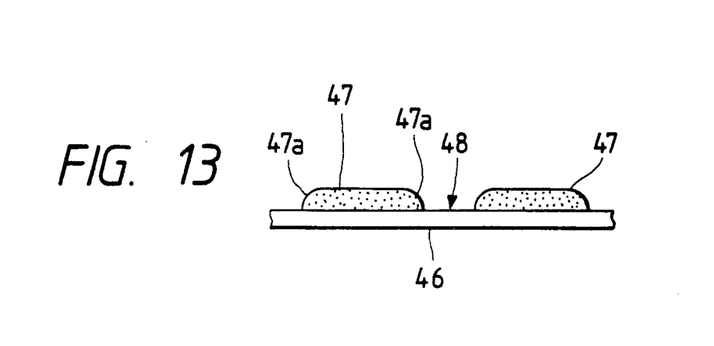
FIG. 13 is a side view showing a blood model of the pulsation generating section of the embodiment shown in FIG. 11.

In FIGS. 11, 12, a disk-like rotating plate 46 is secured to a tip of a rotating shaft 45 that is connected to the output shaft of a motor of the drive section 6, and a plurality of blood models 47 are bonded to outer peripheral portions of the upper surface of the rotary plate 46 to thereby constitute the pulse generating section 48. Each blood model 47 is cut out so that the profile of its end portions 47a is curved to allow a detection waveform close to a pulse wave of a living body to be extracted from the light-emitting section 16.

This rotating plate 46 is fitted into a groove portion 50 cut out on a tissue model 49 horizontally, and is rotated within the tissue model 49 by driving the motor. When the motor is being driven, each of the plurality of blood models 47 on the rotating plate 46 traverses in sequence the space between the light-emitting section 15 and the light-receiving section 16 of the measuring probe 3, so that pulsation can be simulated.

Figure 14:
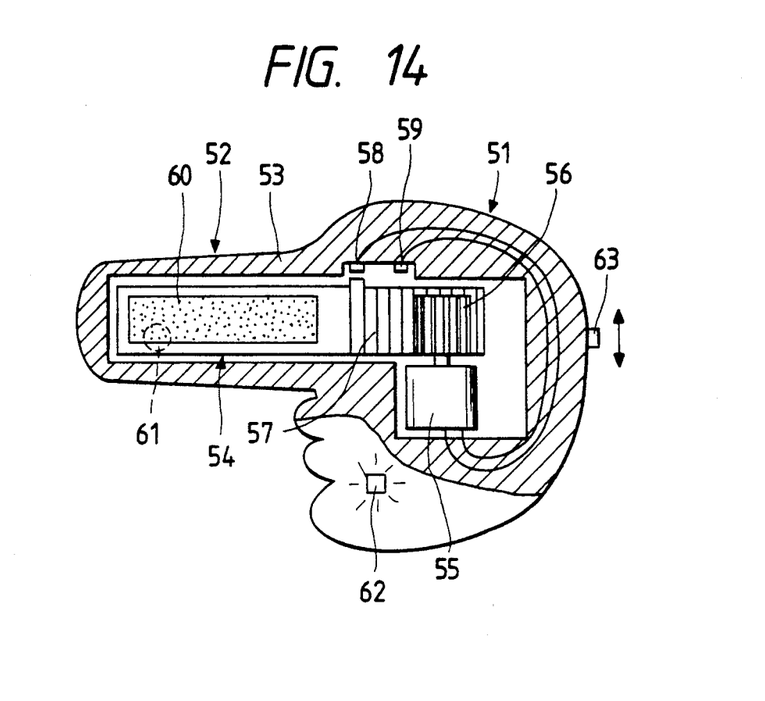
FIG. 14 is a sectional view showing a finger model of a calibration apparatus, which is still another embodiment of the present invention.
Figure 15:
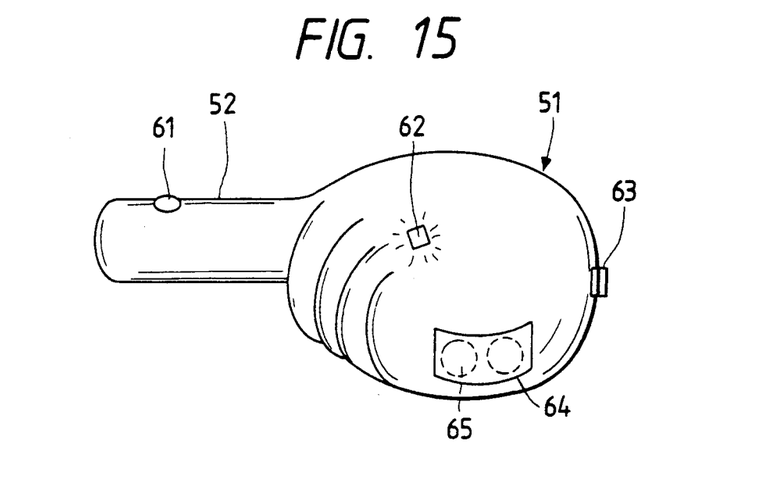
FIG. 15 is a bottom view of the finger model shown in FIG. 14.

A finger model of a calibration apparatus, which is still another embodiment of the invention shown in FIGS. 14 and 15, will be described next. In this embodiment, a model body 51 of human hand is arranged integrally with a finger model 52. The finger model 52 consists of a tissue model 53 and a pulsation generating section 54 that shuttles within the tissue model 53. Within the model body 51 is a drive mechanism for driving the pulsation generating section 54 provided. This drive mechanism includes a gear 56 mounted on the output shaft of a motor 55 and a rack 57 coupled to the substrate of the pulsation generating section 54 and meshed with the gear 56. In this arrangement, upon rotation of the motor 55, the rack 57 to be engaged with the gear 56 causes the pulsation generating section 54 to linearly move in the direction of the finger model 52. Within the model body 51 are also two position sensors 58, 59 for sensing the moving stroke of the pulsation generating section 54. The direction of rotating the motor 55 is reversed based on outputs of these position sensors 58, 59, so that the pulsation generating section 54 to which a blood model 60 is bonded moves back and forth within the finger model 52 in response to each rotation of the motor 55.

Further, the tissue model 53 is provided with a position sensor 61 for detecting the correct installation of the finger model 52 to the measuring probe 3 in reception of light rays from the light-emitting section 15 on the measuring probe 3 side. Upon output of a detection signal from the sensor 61, a set lamp 62 on the body 51 side is turned on. The detection signal from the sensor 61 is used as a permission signal for driving the motor 55. When the detection signal is applied from the sensor 61 while a start switch 63 is being turned on, the motor 55 is driven to cause the pulsation generating section 54 to start shuttling movement.

Further, a battery case 64 arranged below the model body 51 removably accommodates a battery 65 that serves as a driving power source.

The provision of the finger model 52 integrally with the body 51 of a hand model contributes to enhancing the operability when conducting a calibration test of a pulse oximeter.

As described in the foregoing pages, according to the calibration apparatus of the invention, the tissue model is installed to the measuring probe of a pulse oximeter, and the blood model is moved within this tissue model, so that a light-absorbing characteristic approximated to the pulsation of the blood can be simulated.

Therefore, the pulse oximeter can be calibrated using the finger model when conducting a calibration test, thereby contributing not only to improving the repetitivity of measured values for calibration tests, but also to calibrating the pulse oximeter with a high reliability.

What is claimed is:

1. An apparatus for calibrating a pulse oximeter incorporating a measuring probe having a light emitting section and a light-receiving section comprising:
    a tissue model inserted into a space between said light-emitting section and a light-receiving section of said measuring probe;
    a blood model moved within said tissue model; and
    drive means for driving said blood model within said tissue model to traverse said space between said light-emitting section and said light receiving section,
    wherein said tissue model has a light-absorbing characteristic approximated to that of a living tissue and said blood model has a light-absorbing characteristic approximated to that of a blood.

2. An apparatus for calibrating a pulse oximeter as claimed in claim 1, wherein said blood model is shaped as a plate member having a longitudinal axis and an end portion of said blood model is curved in a direction along said longitudinal axis.

3. An apparatus for calibrating a pulse oximeter as claimed in claim 1, wherein said blood model is shaped as a plate member and an end portion of said blood model is curved in a direction which is transverse to said longitudinal axis.

4. An apparatus for calibrating a pulse oximeter as claimed in claim 2, wherein said end portion of said blood model enters into said space between said light-emitting section and light receiving section.

5. An apparatus for calibrating a pulse oximeter as claimed in claim 1, wherein said drive means drives a substrate supporting said blood model in linear motion.

6. An apparatus for calibrating a pulse oximeter as claimed in claim 1, wherein said drive means drives a substrate supporting said blood model in rotary motion.

* * * * *